United States Patent [19]

Erpelding

[11] 4,449,700

[45] May 22, 1984

[54] METHOD AND APPARATUS FOR SAMPLING OR MEASURING A PARAMETER OF A METAL MELT

[75] Inventor: Jean Erpelding, Hautcharage, Luxembourg

[73] Assignee: Arbed S.A., Luxembourg, Luxembourg

[21] Appl. No.: 443,633

[22] Filed: Nov. 22, 1982

[30] Foreign Application Priority Data

Nov. 26, 1981 [LU] Luxembourg .......................... 83789

[51] Int. Cl.³ ............................................. G01F 23/00
[52] U.S. Cl. ....................................... 266/79; 266/88; 266/89
[58] Field of Search ..................... 266/78, 79, 94, 88, 266/89, 86, 99, 90, 92, 93, 80, 87, 100, 91, 96, 97; 75/60; 73/290 R, 291, 292, DIG. 9

[56] References Cited

U.S. PATENT DOCUMENTS 3,708,159  1/1973  De Bray .............................. 266/94
4,003,260  1/1977  Catoal .............................. 73/DIG. 9
4,102,190  7/1978  Fradeneck et al. .................. 266/99

FOREIGN PATENT DOCUMENTS 2718860  11/1978  Fed. Rep. of Germany ........ 266/88
348621   9/1971   U.S.S.R. ............................ 266/79

OTHER PUBLICATIONS

Siemens "*Galvanomagnetic Devices*", Data Book 1976.
Ahrendt et al., "*Servomechanism Practice*", 2nd Edition, pp. 65-84, 1960.

Primary Examiner—L. Dewayne Rutledge
Assistant Examiner—S. Kastler
Attorney, Agent, or Firm—Karl F. Ross; Herbert Dubno

[57] ABSTRACT

The buoyancy change of a probe as it is lowered into a molten metal melt is detected and the lowering of the probe terminated a predetermined time after the detection of the buoyancy change to precisely position the probe at a predetermined level below the surface of the melt without the need for a contact detector which actually touches the melt.

8 Claims, 8 Drawing Figures

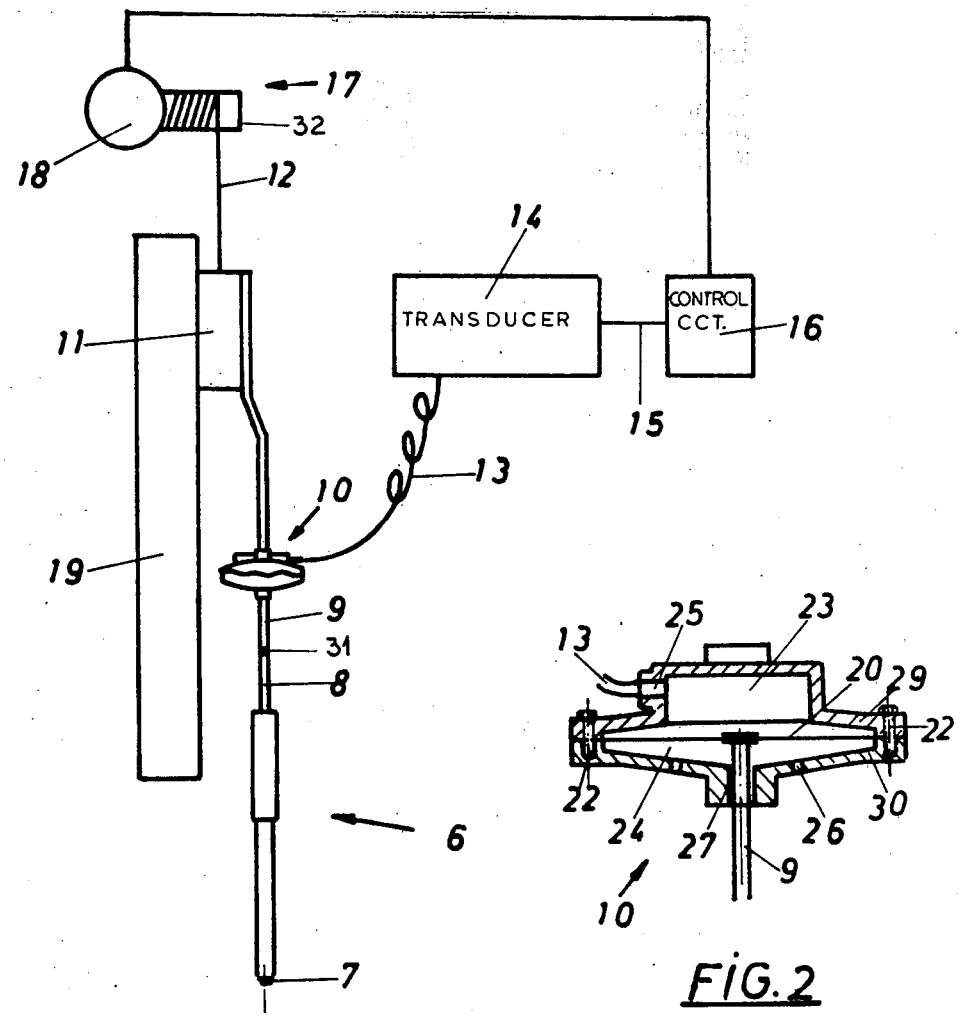
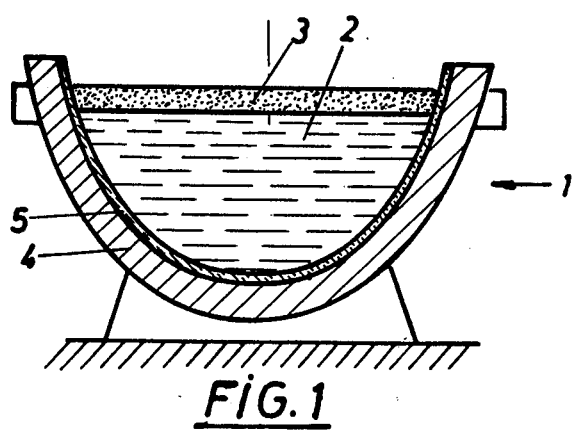

METHOD AND APPARATUS FOR SAMPLING OR MEASURING A PARAMETER OF A METAL MELT

FIELD OF THE INVENTION

My present invention relates to a method of and to an apparatus for measuring a parameter of a metal melt below the surface thereof and/or for sampling the melt, i.e. removing a portion of the melted metal from a location in the metal bath below its surface. More particularly, the invention deals with improvements in monitoring the condition of the molten metal during the refining thereof, especially in the refining of iron and steel.

BACKGROUND OF THE INVENTION

During the course of metallurgical operations, especially the refining of ferrous metals, namely iron and steel, it is frequently necessary to monitor the condition of the melt at a location below the surface thereof.

Such monitoring operations can take the form of a measurement of a parameter of the melt, e.g. its temperature, or the form of a sampling of the melt, i.e. the withdrawal of a portion thereof for subsequent analysis.

Such monitoring may be carried out fairly frequently and is utilized to follow the refining operation and to ensure optimum refining conditions for the highest quality of steel to be produced.

In order that the monitoring be effective, it is important that the samples be representative and taken at the same level or place, i.e. that the sample be withdrawn repeatedly at the same depth of immersion. Even small differences in the level at which the sample is withdrawn can result in errors with respect to the representativeness of the sample, the homogeneity of the product and variations in the refining process and other parameters of the product.

It is thus desirable that temperature measurements, for example, always be made at the same level if they are to be meaningful and any change of temperature is to represent significantly the progress of a refining process, and similarly, that the samples be withdrawn in succession from precisely the same location.

Under the rigorous conditions under which such measurements and sampling must be taken, i.e. extremely high temperatures, evolution of fumes, spattering, turbulence, it is impossible to rely upon an operator to visually control the depth of the sampling or measuring probe.

Consequently, the art has resorted to a mechanization of the sampling or measuring process whereby the descent of a measuring or sampling probe into the bath of molten metal, the duration for which the probe is immersed in the bath and the retraction of the probe from the bath are all controlled by an appropriate mechanism or control system.

For example, in automatic probe installations known heretofore, the descent of the probe is generally arrested at the same position with respect to a fixed reference. The disadvantage of this system, of course, is that it is not amenable to use with various receptacles of different depths or capacities or even shapes since the surface of the bath may be different in each case and the position at which the probe stops may not be meaningful for one or another type of receptacle.

Furthermore, even for a given receptacle the effective use of this system requires that the level of the bath surface always be the same. The level of the surface of the bath, however, is a function of a number of factors, including the quantity of metals charged, the introduction of additives, the tapping of metal or slag which can cause the surface level to vary from refining process to refining process and thereby prevent effective use of this earlier system.

Another system, attempting to overcome these disadvantages, is known from the open German application DE-OS 2,455,670 which utilizes a contact detector fixed on the probe carrier and which terminates the descent of the probe when the detector comes into contact with the superficial surface of the bath.

This detector is generally disposed at a fixed distance from the end of the probe, this distance corresponding to the depth of immersion.

While this arrangement overcomes a problem arising from variations in the position of the surface of the bath, it introduces a number of new problems. For example, it requires the mounting of an auxiliary element, namely the detector, on the side of the probe which may not be convenient, may create mechanical problems with the probe and certainly introduces new operations which can delay the sampling.

Generally, the detector can only be affixed at a given distance from the end or head of the probe so that the assembled apparatus can be used only for a single depth of immersion. The versatility of the arrangement is drastically limited by the fact that one cannot select the depth of immersion at will.

Furthermore, the detector is destroyed at each immersion of the probe into the bath, thereby requiring its replacement.

OBJECTS OF THE INVENTION

It is the principal object of the present invention to provide a method of monitoring the condition of a molten metal bath and an apparatus for such monitoring which obviate the disadvantages of earlier techniques and permit sampling at precisely defined levels which, however, can be easily adjusted.

Another object of my invention is to provide an apparatus for the purposes described which eliminates the need to provide a contact detector on the outside of the probe and hence the need for replacement of this detector because of damage thereto by the molten metal bath.

It is also an object of the invention to provide an apparatus which is simple, easily maintained and accurate in indicating the depth of immersion of the probe.

Still a further object of the invention is to provide an improved method of operating a probe for immersion in a molten metal bath so that the depth of immersion can be precisely established.

SUMMARY OF THE INVENTION

These objects and others which will become apparent hereinafter are attained, in accordance with the present invention, by providing the probe with a detector responsive to the apparent weight of the probe and thereby signaling contact of the probe with the molten metal of the bath as soon as a buoyancy effect by the molten metal on the probe alters the apparent weight.

Furthermore, since the buoyancy effect changes with increasing immersion, it can be used to represent the precise depth of the probe or, if desired, the detection of the initial contact with the bath can permit an automatic control system to advance the probe further to a predetermined, adjustable degree, thereby actually establishing the depth of the immersion of the probe in the bath. Alternatively and in the preferred mode of the invention, a time-delay circuit responds to the detection of contact and halts the descent of the probe at a precisely predetermined interval after contact.

According to a feature of the invention, the probe is mounted at the end of a rod which is suspended from its top by suspension cables connecting the probe to a winch or the like constituting the means for raising or lowering the probe. Advantageously the contact detector of the invention is integrated in the rod-cable system which connects the probe to the winch. The latter can be driven by an electric motor.

The system of the present invention has numerous advantages over the prior art systems. Firstly, the contact detector can be spaced greatly from the melt and thus is not affected by the rigorous conditions present in the region of the melt. The detector can be utilized with various probes and can select the depth to which the probes are lowered since the depth does not depend upon how the probe is connected to its suspension system or the nature of the probe and the selection of the depth can be effected by simple electrical circuitry.

According to another feature of the invention, the means responsive to the apparent weight of the probe includes a pneumatic unit disposed between the probe and the raising and lowering means, this pneumatic unit comprising a thin membrane mounted between a pair of sleeves defining cavities. One of these cavities can communicate with a pressure sensor for measuring the change of pressure developed therein by deflection of the membrane as the probe corrects the path. The lower cavity can, according to the invention, be maintained permanently at atmospheric pressure while an upper cavity is connected to the pressure measurement device.

Alternatively, the detector includes a current generator such as a piezo-electric unit or is an inductive, capacitive, optical, resistive, or Hall effect detector.

BRIEF DESCRIPTION OF THE DRAWING

The above and other objects, features and advantages of the present invention will become more readily apparent from the following description, reference being made to the accompanying drawing in which:

FIG. 1 is a diagrammatic vertical elevational view, showing the ladle in a cross section, illustrating device for taking measurements or samples from a predetermined level of a molten metal bath;

FIG. 2 is a detail view in axial section and also in highly diagrammatic form of the contact detector used in FIG. 1;

SEPCIFIC DESCRIPTION

Figure 3:
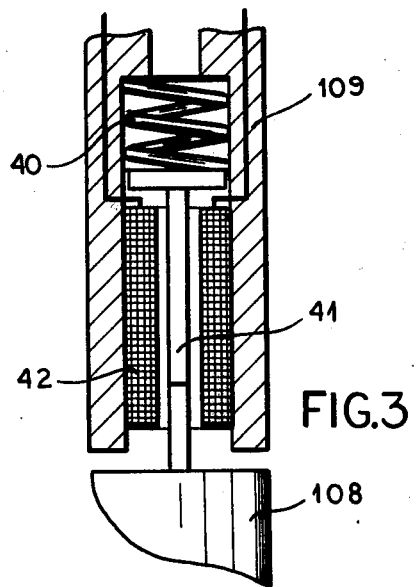
FIG. 3 is a diagrammatic section illustrating another contact detector utilizing inductive principles.

FIG. 1 of the drawing shows a receptacle 1 containing a molten metal bath 2 covered by a slag layer 3. While a refining ladle is here constituted as the receptacle, it is understood that practically any molten metal container, including a transfer ladle, a torpedo ladle, an ingot mold or any other structure adapted to receive molten metal from which a measurement or sample can be taken, can be used in accordance with the principles of the invention.

The ladle 1 has a steel shell 4 lined with a refractory material 5.

The probe 6, suspended above the melt, has a friction fit on a rod 8.

This rod has a diameter which is a function of the type of probe used and is in contact with the latter over a certain portion of the length of the probe and the rod to assure a proper fit.

The probe itself is normally constituted by a cardboard tube closed by a plug 7 of a fusible metal, this assembly enclosing an evacuated sampling receptacle or a temperature measuring head. When the probe is lowered into the melt, the cap 7 melts and uncovers the receptacle permitting a sample to be aspirated into the sample tube or exposing the temperature sensor to provide a temperature indication.

The rod 8 is easily replaceable and is fixed by a quick release connector 31 to a rod 9 directly attached to the contact detector 10. A flexible tube 13 connects the detector 10 to the pressure/voltage transducer 14 forming part of a control circuit of conventional design.

The signal, e.g. in the form of a voltage as is the case with a pressure/voltage transducer or in the form of an electric current as in the case of other detectors to be described, can be amplified and delivered to a cable 15 and thence to the circuit 16. The latter can be a conventional servomechanism (see *Servomechanism Practice*, McGraw-Hill Book Company, New York, 1960, pages 44 ff.) which can control the electrical power winch 17, once the probe has contacted the surface to advance the probe to a predetermined depth.

The motor 18 of the winch 17 pays out a cable 12 from a drum 32 and permits the assembly to lower while being guided by a carriage 11 on a vertical rail 19. The speed of raising and lowering of the probe is controlled by the motor 18.

The speed of the descent, of course, must be sufficiently high to prevent fusion of the cap 7 before the lower end of the probe reaches the desired level in the melt. The speed is normally several tens of meters per minute.

In FIG. 2 I have shown the contact detector of FIG. 1 in greater detail.

The rod 9 passes into a housing body 30 through a boss 27 and is fixed at its upper end to a thin metal membrane 20 of a thickness of several tenths of a millimeter. The membrane is mounted between the two housing bodies 29 and 30 and defines upper and lower chambers 23 and 24 therewith. The two bodies 29 and 30 are sealed against one another and clamp the membrane 20 between them via bolts 22 angularly equispaced about the housing.

Passages 26 in the lower housing member 30 maintain the chamber 24 continuously at atmospheric pressure.

The variations of pressure prevailing in chamber 23 are communicated via passage 25 and the previously described flexible tube 13 to the transducer 14. This transducer can also be mounted on the housing 29, 30 thereby permitting a rigid tube and the sample passage to be substituted for the flexible tube 13.

Still other alternative systems for the contact device have been shown in FIGS. 3 through 8. For example, in FIG. 3 the upper rod 109 is connected to the lower rod 108 by a spring 40 and a core 41 which consists in part only of magnetically permeable material so that the depth to which this material penetrates into a coil 42, forming a linear differential transformer, signals the relative retardation of the downward movement of the rod 108 resulting from the buoyancy effect as the rod 109 is lowered. The principles of such linear differential transformers are discussed at pages 70 ff of *Servomechanism Practice* and, for the purposes of this invention, the linear differential transformer represents any inductive means serving as a contact detector.

Figure 4:
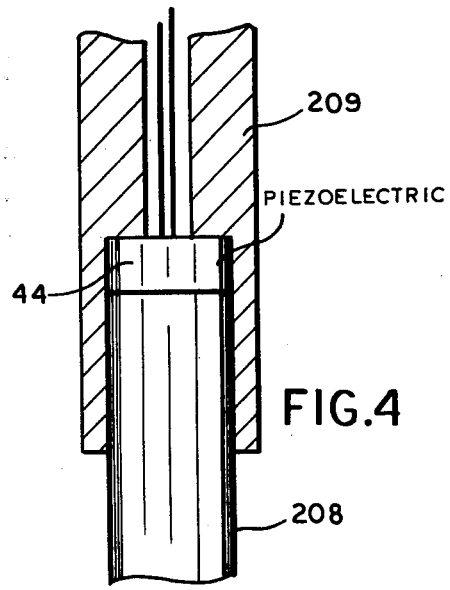
FIG. 4 is a view similar to FIG. 3 showing a contact detector utilizing a piezo-electric element.

In FIG. 4, the rod 208 and the rod 209 are fixed to opposite sides of a piece of electric device 44 whose voltage output also represents the degree of retardation of the lower ring of the rod 208 and hence the probe relative to the lower ring of the rod 209. A resistive unit for similar purposes has been shown in FIG. 5 where the ladle 309 is connected to the rod 308 by the spring 340, the rod 308 carrying a wiper 341 engaging a resistor 45 and thereby forming a potentiometer therewith whose output can be used as a position indicator representing the relative position of the rods and hence retardation of distance of the lower row relative to the upper row.

Figure 6:
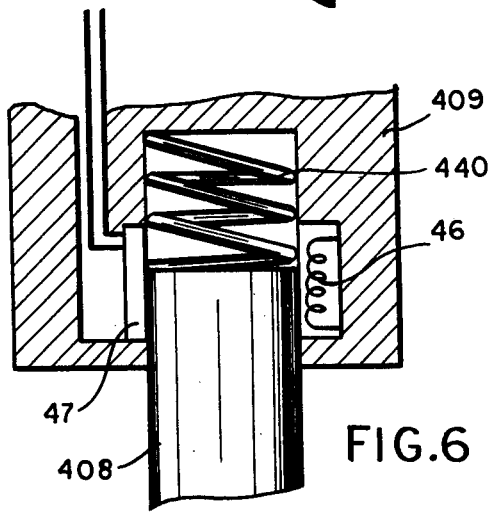
FIG. 6 is a detail section of a contact detector utilizing optical electronic means.
Figure 5:
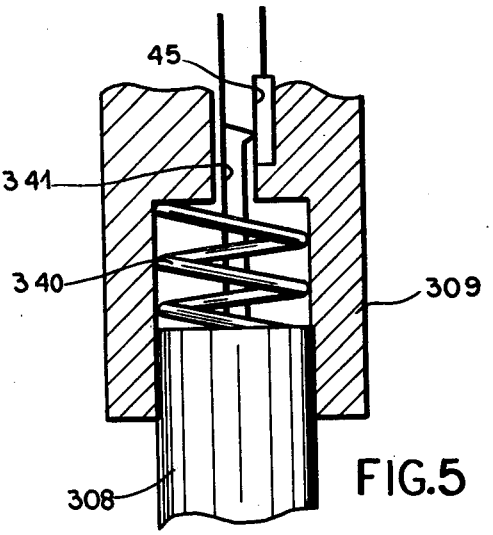
FIG. 5 is another view similar to FIG. 3 showing a contact detector based upon resistive principles.
Figure 7:
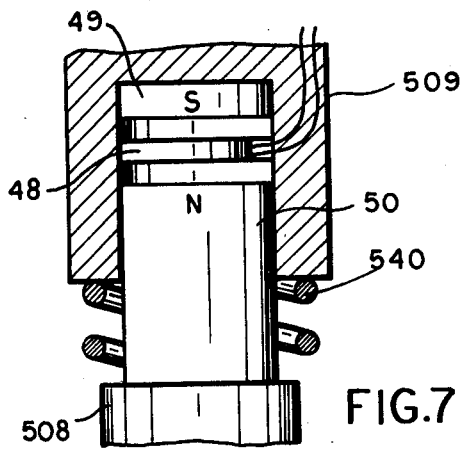
FIG. 7 shows a contact detector in a similar view utilizing the Hall effect.

An optical device can likewise be used for this purpose as can be seen from FIG. 6 where the upper rod 409 is connected to the lower rod 408 by the spring 440 and the lower rod partly obstructs an optical path from a light source 46 to a photoresistor 47 connected in a position sensing circuit.

The Hall effect detector or Hall generator 48 (see *Galvanomagnetic Devices*, Siemens AG, Germany, 1976/1977, pages 23 ff.) may be received between permanent magnets 49 and 50 on the rods 509 and 508 connected by a spring 540 so that the output of this transducer will signal relative movements of the two rods.

Figure 8:
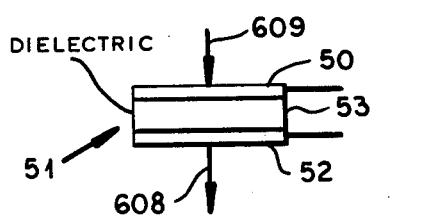
FIG. 8 is a diagram of a capacitive contact detector for use in the system of the invention.

When, moreover, as in FIG. 8, the upper rod 609 carries the upper plate 50 of a capacitor 51 having a lower plate 52 and a compressible dielectric spacer 53, the change in relative positions of the two rods 609 and 608 will be represented by a change in capacitance resulting from compression of the dielectric 53 and the reduction of the dielectric gap spacing.

Before operating, the probe 6 is suspended several meters above the metal bath and because of the weight of the probe and the rod it is fed downwardly as is the case with each of the other detectors described.

The probe is thus lowered under its own weight controlled by the winch at a speed say of 1 meter per second. The impact of the probe against the slag retards the lower rod relative to the upper rod or the housing of the contact detector 10, thereby signaling contact of the probe with the melt.

In the case of the embodiment of FIGS. 1 and 2, impact is transmitted to the membrane 20 which is driven upwardly relative to the housing and compresses the volume in chamber 23 thereby generating a pressure increase to a pressure $P_1$ which is applied to the transducer 14 and thereby generates an electric signal which is delivered to the delay circuit 16. When the head of the probe enters the more dense liquid metal 2, there is again a retardation of the lower rod and an increase in the pressure to a still high level $P_2$. The ratio of the two pressures ($P_1$, $P_2$) represents a measure of the consistency of the slag. This measurement may be valuable in many cases.

In the other embodiments described similar values are obtained. For example, upon entry into the molten metal, the pressure on the piezoelectric crystal 44 is sharply increased and the change in output voltage at this crystal is also a measure of the slag consistency.

In all of the embodiments, moreover, the spacing of the two signals as a function of time, represents the thickness of the slag layer since the velocity of the probe is known.

If it is desired to sample the melt at a depth of 50 cm, for example, from the interface of the slag with the molten metal, the motor 18 is stopped one-half second after the second signal is received. In general, one should also take into consideration the inertia of the system and thus can energize the motor brake less than half a second after the second signal is received. The depth can be selected easily by simply modifying the response circuitry.

However, modifications in the contact detector can be used to detect the instant of contact of the descending probe with the molten metal. For example, a strain gauge on the cable, a torque sensor on the drum or any other device sensitive to a load change represented by the effect of the buoyancy encountered by the probe as it is lowered may be used.

I claim:

1. An apparatus measuring the temperature of a molten metal bath or sampling same at a location beneath the surface thereof, comprising:
    a probe immersible in said bath;
    means for lowering said probe into said bath, said means being connected to said probe;
    a contact detector between said means and said probe responsive to the buoyancy of said probe as it contacts said surface; and
    means connected and responsive to said contact detector for controlling the means for lowering said probe to position said probe at a predetermined depth below said surface, said contact detector including a capacitive device.

2. An apparatuus measuring the temperature of a molten metal bath or sampling same at a location beneath the surface thereof, comprising:
    a probe imxersible in said bath;
    means for lowering said probe into said bath, said means being connected to said probe;
    a contact detector between said means and said probe responsive to the buoyancy of said probe as it contacts said surface; and
    means connected and responsive to said contact detector for controlling the means for lowering said probe to position said probe at a predetermined depth below said surface, said contact detector including an optical device.

3. An apparatus for measuring the temperature of a molten metal bath or sampling same at a location beneath the surface thereof, comprising:
    a probe immersible in said bath;
    means for lowering said probe into said bath, said means being connected to said probe;
    a contact detector between said means and said probe responsive to the buoyancy of said probe as it contacts said surface; and
    means connected and responsive to said contact detector for controlling the means for lowering said probe to position said probe at a predetermined depth below said surface, said contact detector including a Hall effect device.

4. An apparatus for measuring temperature or sampling at a predetermined location below the surface of a molten metal melt comprising:

an upwardly open receptacle receiving said melt;

a probe adapted to be lowered into said melt to said location;

guide means above said receptacle forming a terminal path and including a carriage shiftable upwardly and downwardly along said path;

an electrically operated winch having a cable connected to said carriage for raising and lowering said probe;

a rod connecting said probe to said carriage and having upper and lower portions;

a contact detector responsive to retardation of said lower portion of said rod relative to the upper portion of said rod as said probe is lowered into contact with said surface for controlling said winch;

melt sampling means on said rod for measuring temperature or taking a sample at said location, said contact detector including a transducer generating an electric signal; and circuit means between said transducer and said winch for halting said winch a predetermined time interval from the generation of the signal at said transducer on contact of said probe on said surface, said contact detector also including a housing formed on said upper portion and provided internally with a membrane connected to said lower portion, said membrane subdividing said housing into a pair of compartments, one of said compartments being connected to said transducer.

5. The apparatus defined in claim 4 wherein said transducer is a pressure/voltage transducer spaced from said housing and connected thereto by a flexible membrane.

6. The apparatus defined in claim 5 wherein the upper one of said compartments is connected to said transducer.

7. The apparatus defined in claim 6 wherein the lower one of said compartments is vented to the atmosphere.

8. The apparatus defined in claim 7 wherein the probe is provided with means for sampling the melt.

* * * * *